United States Patent [19]
Kelman et al.

[11] Patent Number: 5,591,233
[45] Date of Patent: Jan. 7, 1997

[54] METAL/COMPOSITE HYBRID ORTHOPEDIC IMPLANTS

[75] Inventors: David C. Kelman, Winona Lake, Ind.; Joseph D. Trentacosta, Wilmington, Del.

[73] Assignee: Depuy Dupont Orthopaedics, Warsaw, Ind.

[21] Appl. No.: 442,072

[22] Filed: May 16, 1995

Related U.S. Application Data

[63] Continuation of Ser. No. 271,540, Jul. 7, 1994, abandoned, which is a continuation of Ser. No. 823,076, Jan. 14, 1992, abandoned, which is a continuation of Ser. No. 531,652, Jun. 1, 1990, abandoned.

[51] Int. Cl.$^6$ ........................................ A61F 2/28
[52] U.S. Cl. ........................... 623/16; 623/18; 623/22; 623/23; 606/76
[58] Field of Search ...................... 623/16, 18, 22, 623/23; 606/76, 77, 78

[56] References Cited

U.S. PATENT DOCUMENTS

| | | | |
|---|---|---|---|
| 2,719,522 | 10/1955 | Hudack | 623/22 |
| 3,772,709 | 11/1973 | Swanson | 623/18 |
| 4,164,794 | 8/1979 | Spector et al. | 623/22 |
| 4,280,233 | 7/1981 | Raab | 623/20 |
| 4,662,887 | 5/1987 | Turner et al. | 623/16 |
| 4,728,335 | 3/1988 | Jurgutis | 623/23 |
| 4,750,905 | 6/1988 | Koeneman et al. | 623/22 |
| 4,790,852 | 12/1988 | Noiles | 623/23 |
| 4,822,366 | 4/1989 | Bolesky | 623/20 |
| 4,892,551 | 1/1990 | Haber | 623/23 |
| 4,892,552 | 1/1990 | Ainsworth et al. | 623/23 |
| 4,921,500 | 5/1990 | Averill et al. | 623/22 |
| 4,997,444 | 3/1991 | Farling | 623/16 |
| 5,192,330 | 3/1993 | Chang et al. | 623/18 |
| 5,397,365 | 3/1995 | Trentacosta | 623/16 |

FOREIGN PATENT DOCUMENTS

| | | |
|---|---|---|
| 359457 | 3/1990 | European Pat. Off. . |
| 2595562 | 9/1987 | France . |
| 2933229 | 3/1981 | Germany . |
| 3138848 | 4/1983 | Germany . |
| 3336005 | 4/1985 | Germany . |
| WO85/04323 | 10/1985 | WIPO . |
| WOA87/04916 | 8/1987 | WIPO . |

OTHER PUBLICATIONS

O'Neil, D A, Design and Analysis of Composite Total Hip Replacement Stems, *Cornell University*, 1989.

*Primary Examiner*—Paul B. Prebilic

[57] ABSTRACT

Metal/Composite hybrid orthopedic implants are disclosed that are useful prosthetic devices. The hybrid implant comprises an intraosseous metal portion and an intraosseous composite portion. The composite portion is comprised of filaments nonlinearly disposed to produce a structure of variable modulus along its length. Also disclosed are a variety of means to secure the metal portion to the composite portion. The method of making the various implants is also disclosed.

13 Claims, 6 Drawing Sheets

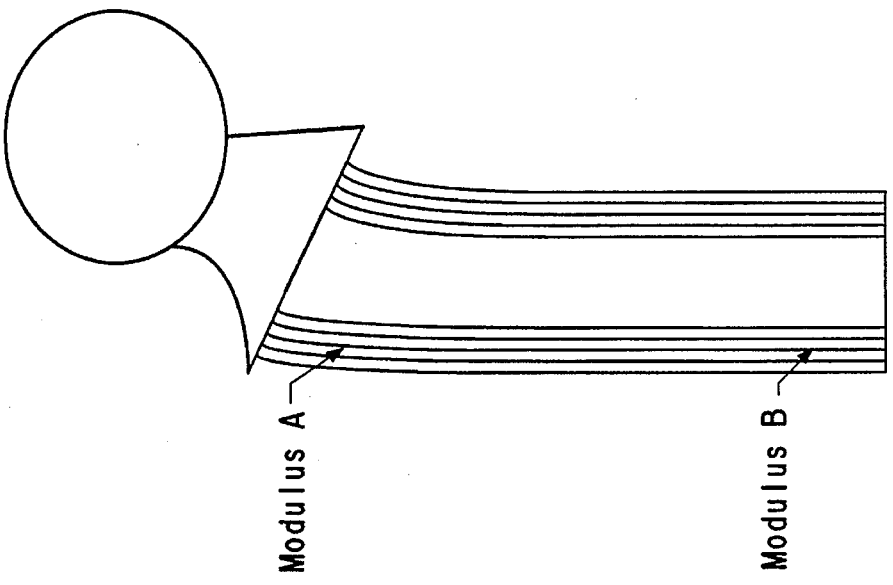
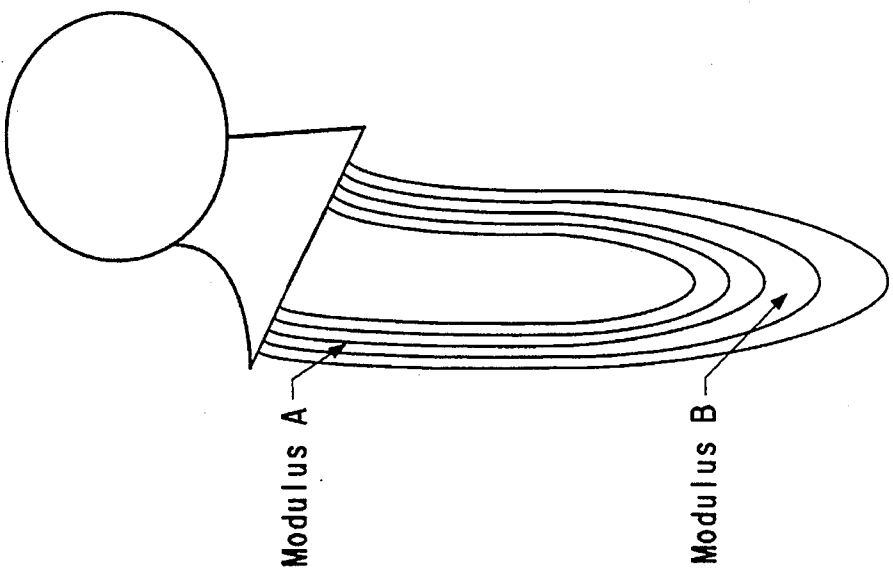
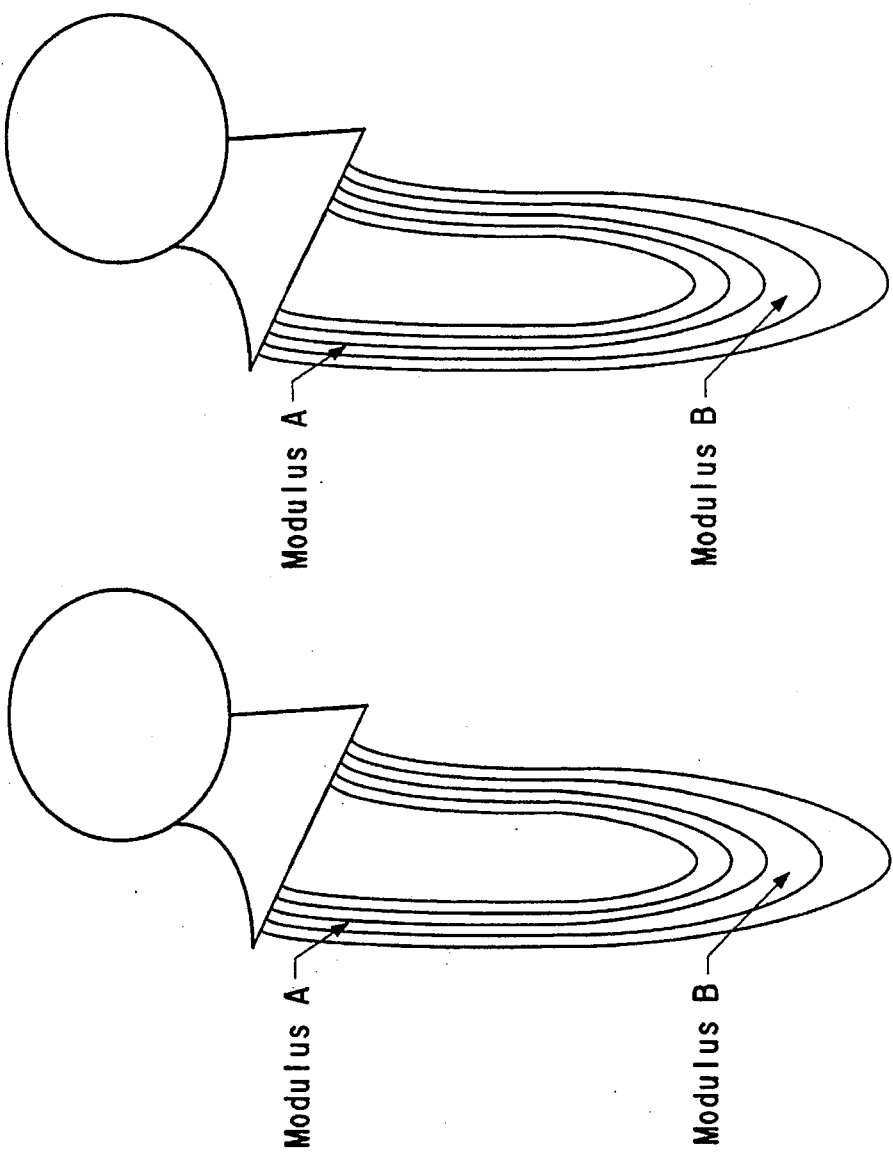

METAL/COMPOSITE HYBRID ORTHOPEDIC IMPLANTS

This is a continuation of Ser. No. 08/271,540 filed Jul. 7, 1994, now abandoned, which is a continuation of Ser. No. 07/823,076 filed Jan. 14, 1992, now abandoned, which is a continuation of Ser. No. 07/531,652 filed Jun. 1, 1990, now abandoned.

FIELD OF THE INVENTION

The present invention relates to orthopedic implants, and more particularly to load bearing prosthetic devices including both metal and composite components.

BACKGROUND OF THE INVENTION

Orthopedic implants include a wide variety of devices, each suited to fulfill particular medical needs. Examples of such devices are hip joint replacement devices, knee joint replacement devices, shoulder joint replacement devices, and pins, braces and plates used to set fractured bones. Particular emphasis has been recently placed on hip joint prosthetic equipment. A typical configuration for a hip joint prosthetic includes a proximal region and a distal region. The proximal region has a ball attached thereto and adapted to engage a cup portion (an artificial socket embedded in the pelvis). The ball is attached via an extension piece called the neck to the body of the proximal region. The body is joined to a distal region, which both extend into the femur.

Contemporary orthopedic implants, including hip and knee components, use high performance metals such as cobalt-chrome and titanium alloy to achieve high strength. These materials are readily fabricated into the complex shapes typical of these devices using mature metal working techniques including casting and machining. Yet, these metals are characterized by high, fixed moduli of elasticities which makes it difficult to achieve optimal device stiffness within a given anatomical geometric envelope. In particular, in regions in which metal implants share load with surrounding bone, e.g. the medullary canal of the femur, the stress in the bone is substantially reduced versus the normal physiological level. This "stress-shielding" effect often leads to bone remodeling and may be implicated in clinical problems such as aseptic loosening and pain. Stress shielding is particularly acute in large metal implant systems. Further, large metal implants require more bone cement and are more susceptible to loosening than smaller implants.

Composite materials offer the potential to achieve high strength in orthopedic devices while permitting the control of stiffness for enhanced load transfer to bone. In particular, the implant designer can control modulus by varying reinforcement type, orientation and amount. Such a device is revealed in PCT patent application WO/85/04323. The device is formed from a composite material of continuous filament carbon fibers embedded within a polymer matrix. The carbon fibers in the composite material are at specific orientations relative to a specific dimension of the orthopedic device. The angularity of the carbon fibers modifies the modulus of the device. To effect fiber orientation, uniplanar sheets of carbon fibers are formed and cut into coupons. The coupons are then stacked into blocks or rolled into cylinders, to be fashioned into the final device. The manner in which the sheets or coupons are oriented will affect final mechanical properties. However, the prosthetic device according to this invention is limited in that the orientation of the carbon fibers cannot be varied along the formed elongated body.

European Patent Publication 0277 727 discloses an orthopedic device of a biocompatible polymer with oriented fiber reinforcement. Prostheses of this reference are formed from plies of continuous filament fibers that are curvilinearly disposed within a body. The plies may have a balanced orientation; that is, for each sheet having fibers offset at a positive angle there is essentially a sheet having fibers offset at about the same negative angle. However, the prosthetic device of this variety is limited in that the orientation of the carbon fibers cannot be varied along the formed elongate body.

U.S. Pat. No. 4,750,905 reveals a prosthesis construction including an elongate, tapered polymer core containing continuous-filament fibers oriented substantially along the length of the core. The core includes an elongate distal stem. A braided sheath encases the stem. The filaments in the braid encircle the core in a helical pattern. However, devices according to this reference cannot be formed in a flexible laydown pattern as in the present invention. Moreover, the device does not reveal the unique means to fasten the proximal body portion to the distal composite portion of the orthopedic device as in the present invention.

It is an object of the present invention to provide a hybrid orthopedic implant wherein the stresses in the surrounding bone are more nearly equal to their normal physiological level than achieved in an all metal system. It is a feature of the present invention to provide a variety of means to secure the intraosseous metal portion to the intraosseous composite portion. It is an advantage of the present invention that the subject orthopedic implants may have a variable modulus along their lengths due to the use of filament winding and braiding techniques.

These and other objects, features and advantages of the present invention will become more readily apparent with reference to the following description of the invention.

SUMMARY OF THE INVENTION

The present invention provides an orthopedic device for human implantation. The device comprises an intraosseous metal portion and an intraosseous composite portion attached thereto. The composite portion comprises one or more filaments disposed about a longitudinal axis and within a polymer matrix.

In the orthopedic device the composite portion may be received within the metal portion and secured thereto. The portions may be secured by a taper lock, an adhesive joint, or a shrink fit joint. Alternatively, in the orthopedic device, the metal portion may be received within the composite portion and secured thereto. In such a case, the metal portion comprises a first extension that is received within the composite portion and a second extension positioned outside the composite portion. This first extension may be secured to the composite portion by a plurality of pins extending radially from the extension. In another embodiment, the second extension is grooved to accommodate a threaded compression nut. A still further means of securing the metal portion to the composite portion is by a shrink fit joint.

The intraosseous composite portion of the orthopedic device may be prepared by several processes of the invention. One such process comprises winding or braiding fiber into a preform and placing the preform into a mold. Thermoset resin is injected and cured.

BRIEF DESCRIPTION OF THE DRAWINGS

FIG. 3 is an exploded view of metal/composite hybrid tibial knee component.

FIG. 13 A and B is a side view of a portion of a metal body joined to a portion of a composite stem by another particular fastening means, first immediately prior to joinder and second immediately after joinder.

FIG. 14 is a side view of a metal/composite hybrid hip implant further including a metal insert placed between the metal portion and the composite portion.

DETAILED DESCRIPTION OF THE INVENTION

The orthopedic devices of this invention are considered to have a wide range of applicability throughout the human body. Thus, the intraosseous metal and composite portions relate generally to any portion of the body where they may be implanted into bone and further where prosthetics are desirable. For example, the devices may be implanted to support rotational movement at the shoulder, knee, hip, and the like. Much attention is focused herein on the relation of the orthopedic device to a hip implant. For this use, the intraosseous metal portion is considered a proximal metal body and the intraosseous composite portion is a distal composite stem. While many of the features of the invention are discussed in the context of a hip implant system, it is intended that the many components of the invention be given the wider applicability to implants throughout the body.

Figure 1:
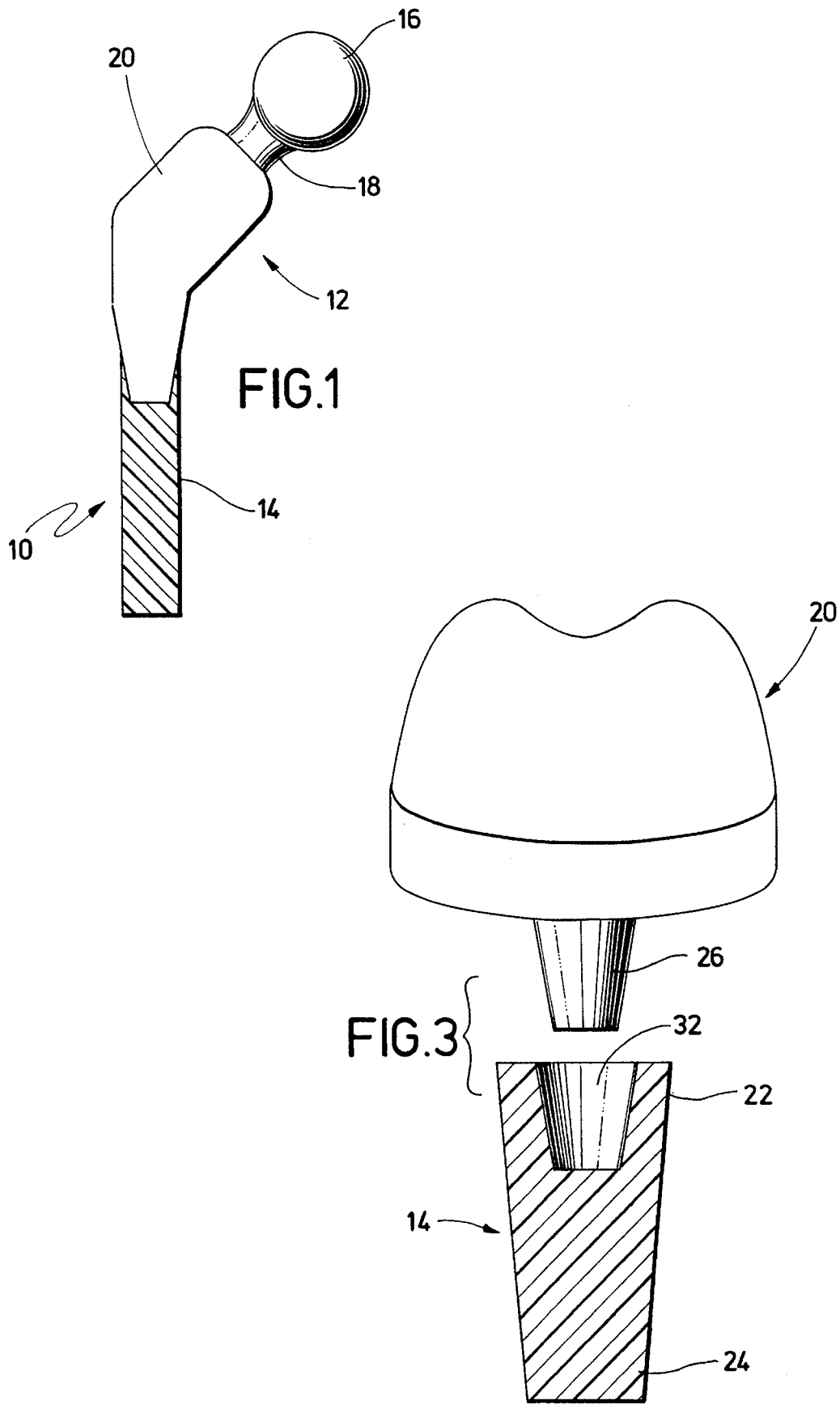
FIG. 1 is a side view of a metal/composite hybrid hip implant in which the metal body is received within the composite stem.

Having reference of FIG. 1, a basic design of a metal/composite hip implant is illustrated at 10. A proximal metal body 20 is attached to a distal composite stem 14. The proximal metal body 12 is connected to a ball 16, via neck 18. The ball 16 is rotatably engaged within a cup of the pelvis (not shown), while the proximal metal body 20 and distal composite stem 14 are positioned within an orifice in the femoral canal (not shown).

The design depicted in FIG. 1 shows the connection between proximal metal body 20 and distal composite stem 14 as comprising an aperture in the stem 14 which receives the metal body 20. Alternatively, an aperture in the metal body 12 may receive the composite stem 14.

Figure 2:
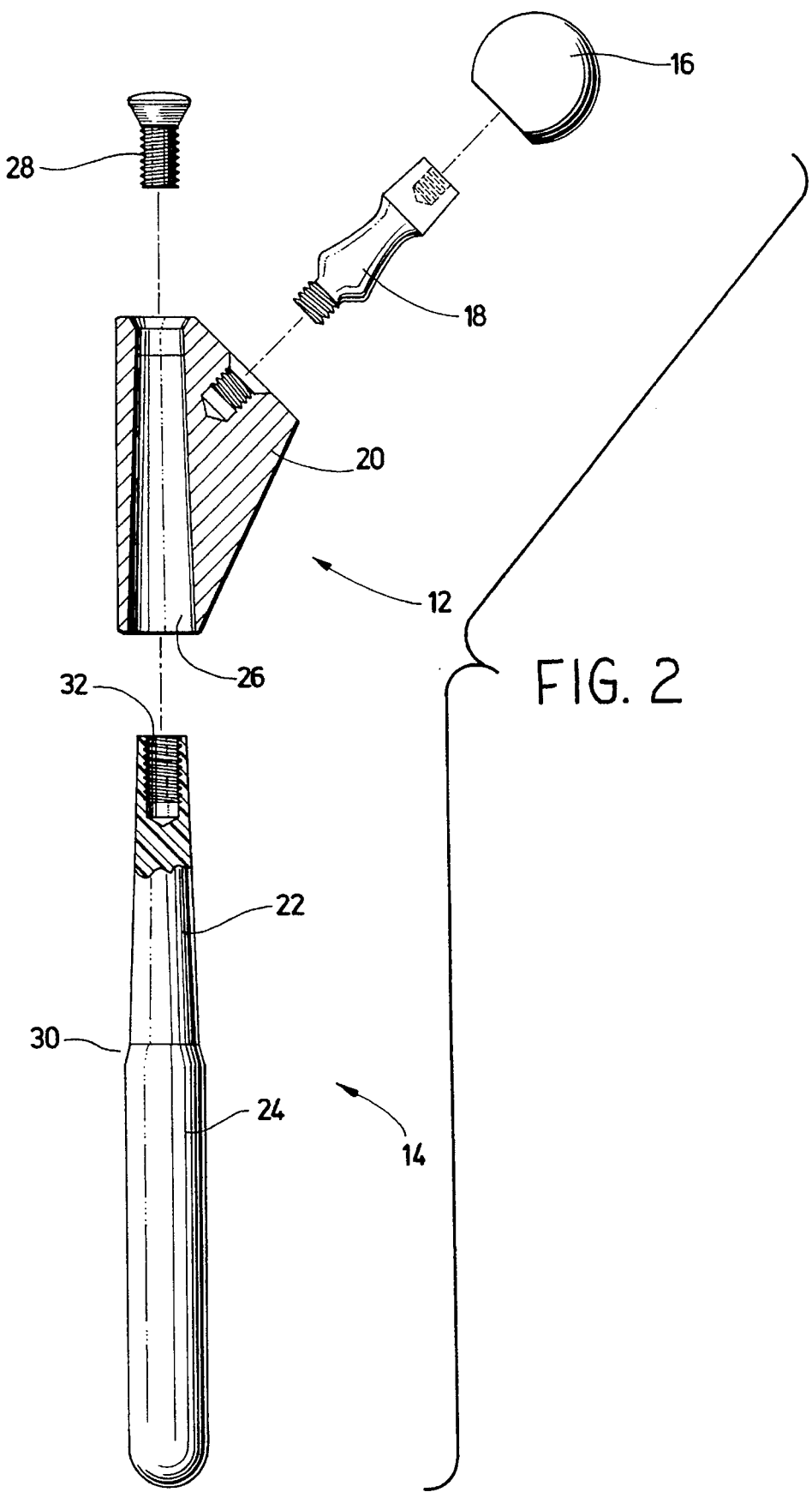
FIG. 2 is an exploded view of a modular hip implant with a composite stem.

The modular hip of FIG. 2 is illustrative of one embodiment of the present invention. The distal composite stem 14 contains a first extension (in this case taper 22) that is received within the proximal metal body 20 and secured by friction (or "press fit"), and a second extension (in this case the untapered region 24) that is located outside of the proximal metal body. Dimensionally, the cross-sectional area of the first extension is different from or equal to that of the second extension. In one embodiment, both extensions are cylindrical. More commonly and as illustrated, the first region forms a taper such that the cross-sectional area of the taper decreases proximally. The untapered region 24 is typically cylindrical in shape with a rounded end. The tapered region 22 is mated to the untapered region 24 by a bevelled transition portion 30. This is because the maximum cross-sectional area of the tapered region 22 may be different from the cross-sectional area of the untapered region 24. The bevelled transition portion 30 has a cross-sectional area equal to that of the tapered region 22 and equal to that of the untapered region 24 at their respective interfaces. The tapered region 22 is received within aperture 26 of the body 20. The aperture 26 is designed to closely follow the contours of the tapered region 22 of stem 14. Thus, tapered region 22 and aperture 26 both form conical patterns with a small diameter at the top increasing progressively toward the bottom. The composite stem 14 is received within the body 20 and the two parts are joined by friction between taper 22 and aperture 26 in a manner commonly called a taper lock joint. The stem 14 and body 20 are secondarily joined by fastening means 28.

Other transition region shapes 30 are possible. The selection of shape is governed by the physical requirements of space and geometry of the device as well as the desired stress concentration for a given composite material.

The modular knee component of FIG. 3 is illustrative of another embodiment of the present invention. The distal composite stem 14 is used with an existing tibial component of an artificial knee. The stem 14 contains an externally tapered region 24 made to be positioned within an orifice in the medullary canal of the tibia. The stem includes a second portion 22 which contains tapered orifice 32 which receives taper 26 in the metal body 20. The stem 14 and proximal metal body 20 are joined by friction between taper 26 and aperture 32.

Figure 4:
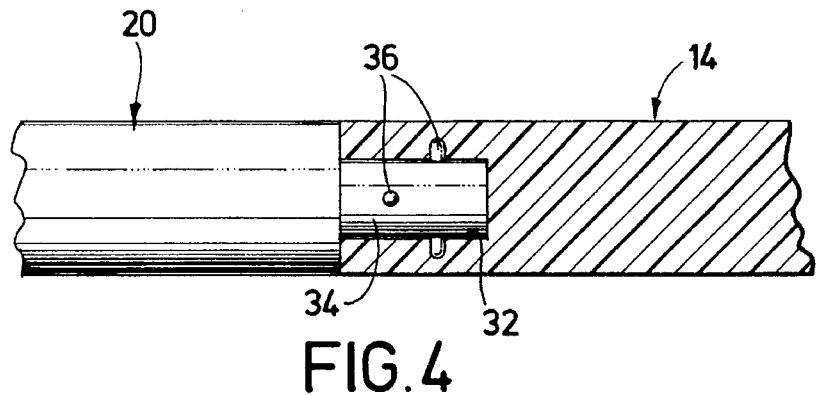
FIG. 4 is a side view of a portion of a metal body joined to a portion of a composite stem by a particular fastening means.
Figure 5:
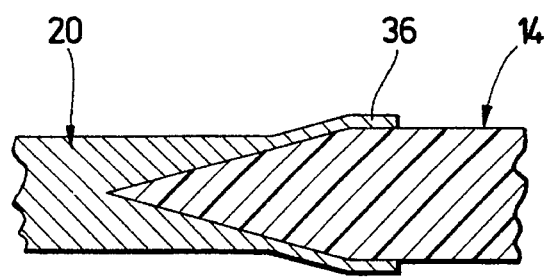
FIG. 5 is a side view of a portion of a metal body joined to a portion of a composite stem by another particular fastening means.
Figure 6:
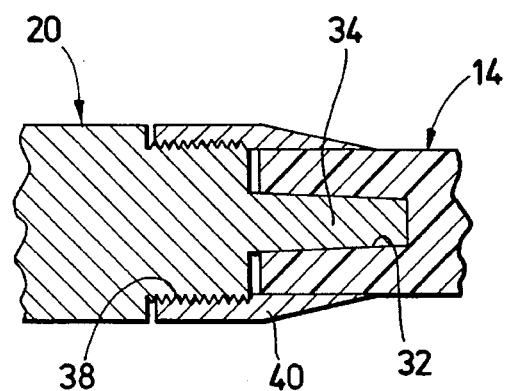
FIG. 6 is a side view of a portion of a metal body joined to a portion of a composite stem by another particular fastening means.

A key issue in metal-composite hybrid systems is the transitive region which joins the two dissimilar materials. Several approaches to the metal-composite joint have been discovered to be useful, and are depicted in various figures. In FIGS. 2 and 3, the metal body 20 is secured to the composite stem 14 via a frictional taper lock joint. Other means are also possible as revealed in FIGS. 4–6. In one design (FIG. 4), body 20 contains an extension 34 including pins 36 emanating radially therefrom. Composite 14 is formed by winding or braiding filaments embedded in a polymer matrix along its longitudinal axis; these filaments envelop the extension 34 and pins 36. In another version (FIG. 5), the body 20 contains a sleeve 36 and the composite stem 14 is shaped to be adhesively received within the sleeve 36. Yet another fastening means (FIG. 6) requires the formation of extension 34 on body 20 to be received within aperture 32 of stem 14 and to have a threaded portion 38 which accommodates compression nut 40.

The shrink fit joint mentioned previously is yet another means to secure the intraosseous metal portion to the intraosseous composite portion, and is illustrated in FIGS. 13 A and B. The shrink fit joint takes advantage of differences in the coefficients of expansion of the metal and composite selected. The components are assembled at a temperature which is different from the temperature at which the orthopedic device will be employed. At a suitable assembly temperature, there is clearance between the metal portion 12 and the composite portion 14 and the two portions are fitted together. At the temperature at which the assembled orthopedic device is used, the dimensional characteristics of the metal portion 12 and the composite portion 14 have changed relative to one another, causing a dimensional interference to secure the portions together.

Another feature of the invention as depicted in FIG. 14 concerns the placement of a metal insert 13 between the intraosseous metal portion 12 and the intraosseous composite portion 14, thus connecting the two portions. The metal insert is tapered and received within the metal portion 12 and secured frictionally in the same fashion as the composite insert described previously. The metal insert is connected to the composite portion 14 by either an adhesive joint or a shrink fit joint. The use of a metal insert enables one skilled in the art to introduce a third material with its own stiffness characteristics into the metal/composite system, to further customize the treatment of stress concentrations and micromotions to fit a particular need.

The proximal region 20 is fabricated by conventional metal working techniques. It may consist of any of a wide variety of metals, the most preferred being stainless steel, cobalt-chrome alloy, and titanium alloy.

The composite stem consists of filaments embedded in a polymer matrix. The filaments are selected from any of a wide variety of candidates, the criteria of selection being ease of manipulation, and compatibility with the polymer matrix. Preferred filaments include carbon, graphite, glass and aramid fiber. The organic matrix is selected according to its compatibility with both the wound filaments and the tissue and other materials with which it comes into contact. The matrix is preferably selected from polysulfone, polyether-ether-ketone, polyether-ketone-ketone, polyimide, epoxy and polycyanate.

An important feature of this invention is the variable modulus along with the length of the composite stem. The equivalent flexural modulus of the portion of the distal stem which interfaces with bone is up to 16 million psi. A preferred range of this modulus is 1 million to 8 million psi.

Thus, according to the invention as described herein, the intraosseous composite portion may further have a gradient in modulus along the length thereof. The composite portion can be described as having a first region that interfaces with the metal portion and a second region that is distal to the metal portion, with the modulus of the first region greater than the modulus of the second region. In a preferred embodiment, the modulus of the first region of the composite portion is greater than or equal to the modulus of the metal portion. In still another preferred embodiment, the composite portion has a gradient in modulus along the length thereof. The incorporates of a gradient modulus within the composite portion finds particular application in hip implant systems.

One method of making an orthopedic device according to the invention comprises the steps of first filament winding or braiding filaments about a longitudinal axis to form a preform comprising one or more layers. Each layer may contain fibers oriented at a constant angle along the longitudinal axis or fibers oriented at a changing angle with the longitudinal axis. The angles used are selected to give desired mechanical properties both globally and locally in the structure. A winding or braiding process which results in a constant angle along the axis is called a linear winding or braiding process. One which results in a changing angle along the axis is called a nonlinear winding or braiding process. The preform is then placed in a mold cavity and a thermosetting resin is injected into the cavity. The preform and the resin are cured to form a distal composite stem, which is removed from the mold.

A second method for making an orthopedic device according to the invention comprises the steps of first coating filaments of a reinforcing fiber with a polymer matrix, preferably a thermoplastic polymer. Then, the coated filaments are wound or braided about a longitudinal axis so as to produce a part comprising layers using a system which welds the coated filaments to the previously wound or braided layers, for example, by application of heat and pressure. Linear or nonlinear winding or braiding processes may be used to create the layers so that the the fibers comprising the layers may lie at a constant or changing angle with respect to the longitudinal axis to give desired global and local mechanical properties. The part formed by this process may be further consolidated in a subsequent process such as molding or autoclaving.

A third method for making an orthopedic device according to the invention comprises the steps of first cutting sheets of reinforced fiber preimpregnated with a polymer matrix, preferably a thermoplastic polymer, such that fiber in each cut sheet is oriented in a prescribed manner. The cut sheets are then stacked in a particular order to give a desired angle pattern throughout the structure which in turn determines the global mechanical properties of the device. A typical ordering of the angles would be designated $[0, \pm\alpha, \pm\alpha 90]_s$, where the 0 denotes orientation parallel to the axis of the part, $\pm\alpha$ denotes orientation at an angle alpha to the axis (alternating between positive and negative angle) and 90 denotes orientation perpendicular to the axis of the part and s denotes the repetition of the pattern to give mirror image symmetry. It is known to those skilled in the art that other ordering of the orientations is possible; for example, one may exclude the 0 or $\pm\alpha$ or 90 components. The resultant stack is then molded using heat and pressure to form a consolidated laminate which is then machined to the final shape of the stem.

Detailed design of the intraosseous composite portion can be based on an analysis of the mechanical loading conditions in the composite portion and the surrounding bone. It is an objective of the present invention to enhance load transfer to the surrounding bone by using a composite vs. a metal distal stem. In particular, the present invention achieves a stress level in the bone closer to the normal physiological level than achieved with conventional all-metal implants.

Figure 7:
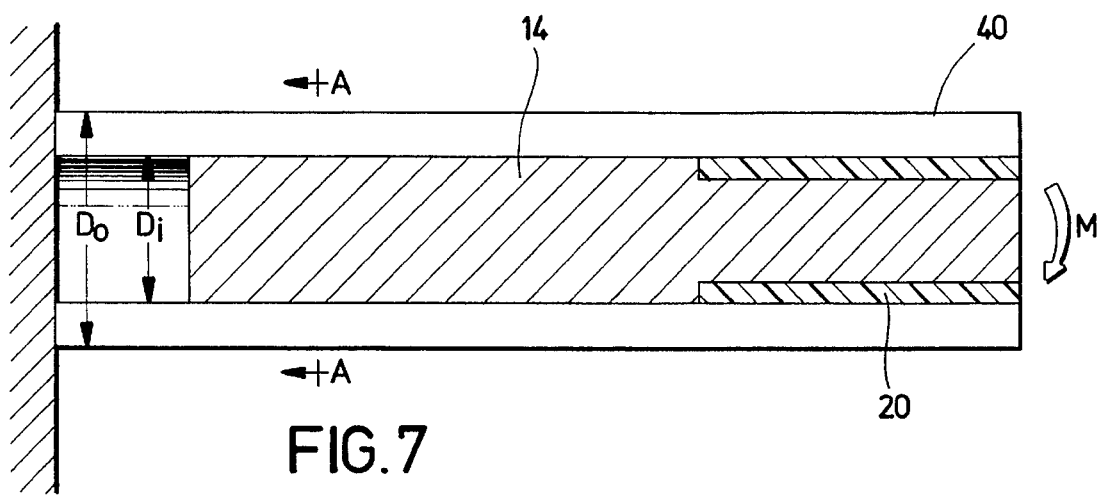
FIG. 7 is a side view of a mechanical idealization of a metal composite hybrid hip implant.
Figure 8:
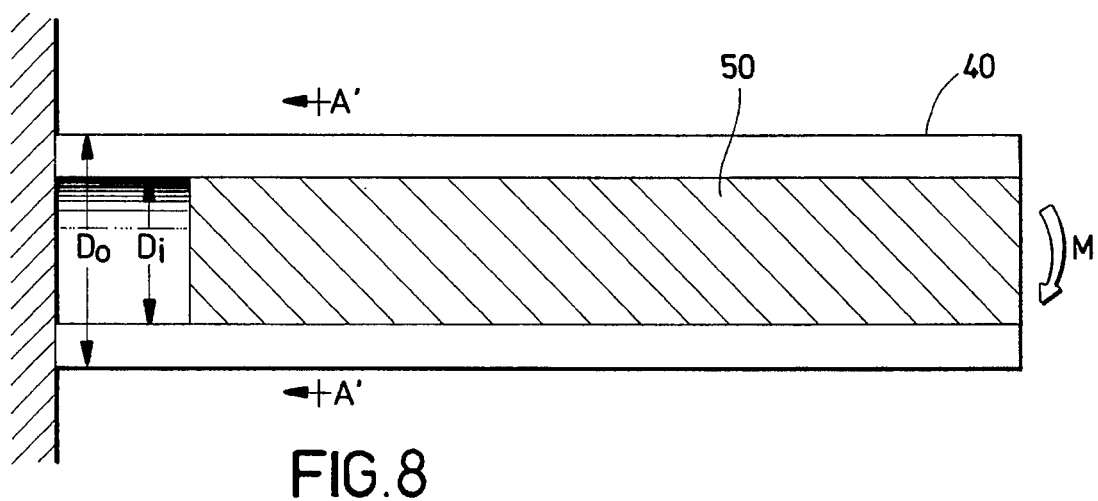
FIG. 8 is a side view of a mechanical idealization of a press fit metal hip implant.
Figure 9:
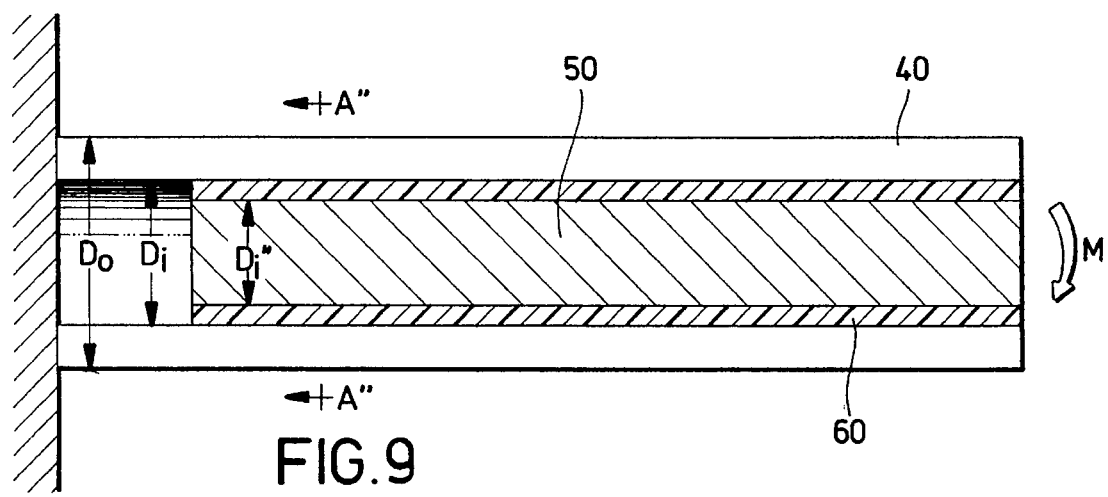
FIG. 9 is a side view of a mechanical idealization of a PMMA grouted metal hip implant.

FIG. 7 shows a mechanical idealization of a hip implant according to the invention in which distal composite stem 14 and proximal metal body 20 are modeled as cylindrical entities fixed within a hollow cylinder of bone 40 representative of the shaft of the femur. For comparison FIG. 8 shows an analogous idealization for an all-metal system 50 press fit into bone 40 and FIG. 9 is are analogous idealization for an all-metal system 50 grouted into bone 40 using polymethylmethacrylate bone cement 60. In all three figures the idealized structure is subjected to bending moment M; bending being the principle mode of loading of hip implant systems.

The following nomenclature is used throughout this discussion:

$D_o$: outer diameter of bone 40

$D_i$: inner diameter of bone 40, and outer diameter of distal portion of stem 14 and outer diameter of stem 50

$D_i''$: outer diameter of PMMA grouted stem 50

$I_b$: moment of inertia of bone 40 cross-section $I_c$: moment of inertia of distal portion of composite stem 14

$I_{c2}$: moment of inertia of proximal portion of composite stem 14

$I_m$: moment of inertia of metal body 20

$I_m'$: moment of inertia of press fit stem 50

$I_m''$: moment of inertia of PMMA grouted stem 50

$I_p$: moment of inertia of PMMA cross section $E_b$: modulus of elasticity of bone 40

$E_c$: modulus of elasticity of distal portion of composite stem 14

$E_{c2}$: modulus of elasticity of proximal portion of composite stem 14

$E_m$: modulus of elasticity of metal $E_p$: modulus of elasticity of PMMA $L_1, L_2, L_3, L_4$: lengths in figures The maximum bending stress in bone 40 at section A—A for the system shown in FIG. 7 is found using mechanics of materials analysis to be $$\sigma_b = \frac{ME_b D_o/2}{E_b I_b + E_c I_c}.$$

This can be compared to the maximum bending stress in the bone without the implant in place $$\sigma_{bo} = \frac{M D_o/2}{I_b}.$$

It is an objective of the current invention to maximize the ratio $\sigma_b/\sigma_{bo}$ by modification of the modulus of elasticity of the composite, $E_c$.

For comparison, the maximum bending stress in bone 40 at section A'—A' for the press fit metal system of FIG. 8 is $$\sigma_b' = \frac{ME_b D_o/2}{E_b I_b + E_m I_m'}.$$

and the maximum bending stress in bone 40 at section A"—A" for the PMMA grouted system of FIG. 9 is $$\sigma_b'' = \frac{ME_b D_o/2}{E_b I_b + E_m I_m'' + E_p I_p}.$$

By forming the ratios $\sigma_b/\sigma_b'$ and $\sigma_b/\sigma_b''$ one can quantify the improvement in load transfer with a composite stem vs. the press fit metal stem and PMMA grouted metal stem. In particular, it is an objective of the current invention that the modulus of the distal composite stem be selected such that these ratios are both greater than 1 signifying that the stress in the bone is greater than that achieved for either the press fit metal stem or the PMMA grouted metal stem. To better define this criteria we consider the following typical values for the parameters defining the mechanical idealizations:

$D_o$=25 to 35 (mm) bone outer diameter $D_i$=12 to 22 (mm) bone inner diameter and composite stem and press fit metal stem diameter $D_i''=(D_i-4)$ (mm) Grouted metal stem diameter $E_b$=2.5 million psi $E_m$=16 million psi for Ti—6Al—4V alloy $E_p$=0.33 million psi The ratio $\sigma_b/\sigma_b'$ was computed as a function of composite modulus up to 16 million psi for each of two bone outer diameters. For all values of $E_c$ less than the modulus of the metal stem, the ratio $\sigma_b/\sigma_b'$ is greater than 1; i.e., the bone stress is always higher in the composite implant system than in the press fit metal system if $E_c<E_m$. Thus, the modulus of a low modulus metal, titanium alloy, is one upper limit for the composite modulus of the invention.

The ratio $\sigma_b/\sigma_b''$ was computed as a function of composite modulus up to a value of 16 million psi. is apparent that for each stem diameter there is a modulus $E_1$ lower than the modulus of the metal at which the ratio $\sigma_b/\sigma_b''$ becomes equal to one. At values of composite modulus lower than $E_1$, the ratio $\sigma_b/\sigma_b''$ is greater than 1. This value of modulus, thus, becomes a more preferred upper limit for the modulus of the composite stem. We state this criteria $E_c \leq E_1$ where $\sigma_b/\sigma_b''=1$ when $E_c=E_1$.

Figure 10:
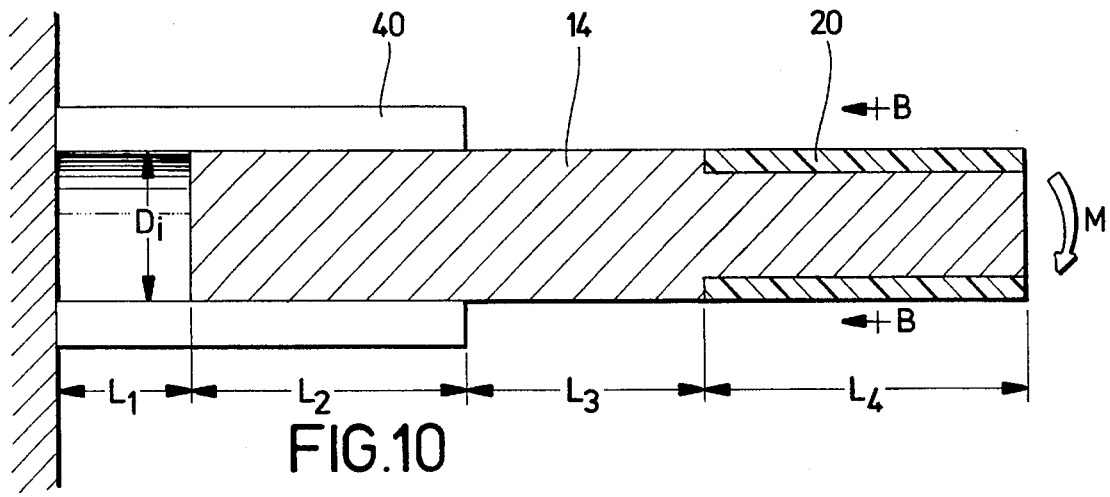
FIG. 10 is a side view of another mechanical idealization of a metal composite hybrid hip implant.

Those skilled in the art will recognize that there are other constraints on a hip implant system which may limit the maximum value of $\sigma_b/\sigma_{bo}$ which can be attained in practice. The stem must, for example, be stiff enough to resist rotatory motion if proximal bone support is lost as modeled in FIG. 10. In this figure the distal stem 14 remains well fixed to bone 40 but the proximal body 20 no longer makes intimate contact with bone. Physiologically, this lack of proximal bone support may typify the immediate post operative period prior to tissue ingrowth into proximal porous fixation means or be representative of the state of the implant years after implantation where bone remodeling has caused loss of bone support. In either case the distal stem 14 must have sufficient rigidity to resist rotatory motion caused by moment M. The rotatory stiffness of the structure in FIG. 10 is given by:

$$S = \frac{1}{\left[\dfrac{L_1}{E_b I_b}\right] + \left[\dfrac{L_2}{E_b I_b + E_c I_c}\right] + \left[\dfrac{L_3}{E_c I_c}\right] + \left[\dfrac{L_4}{E_{c2} I_{c2} + E_m I_m}\right]}$$

Figure 11:
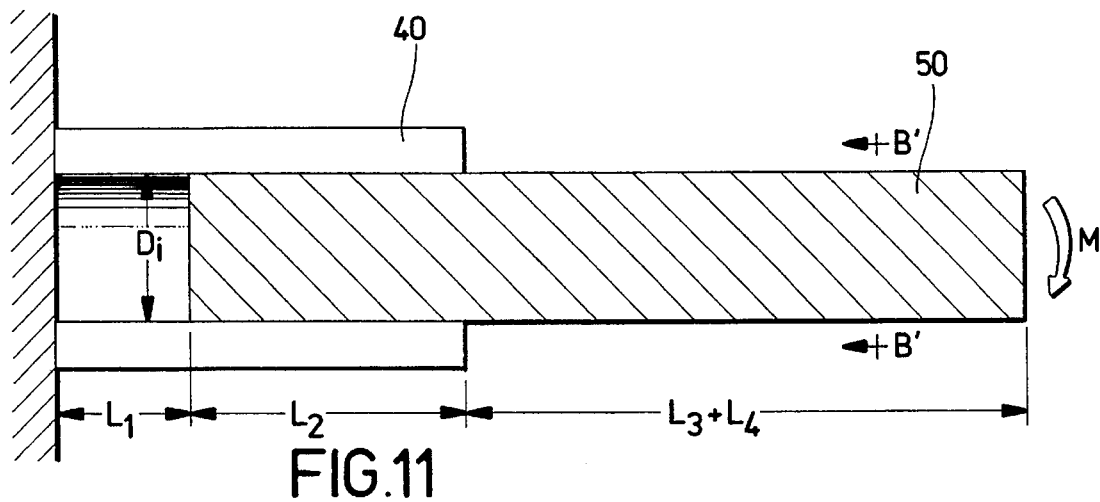
FIG. 11 is a side view of another mechanical idealization of a press fit metal hip implant.
Figure 12:
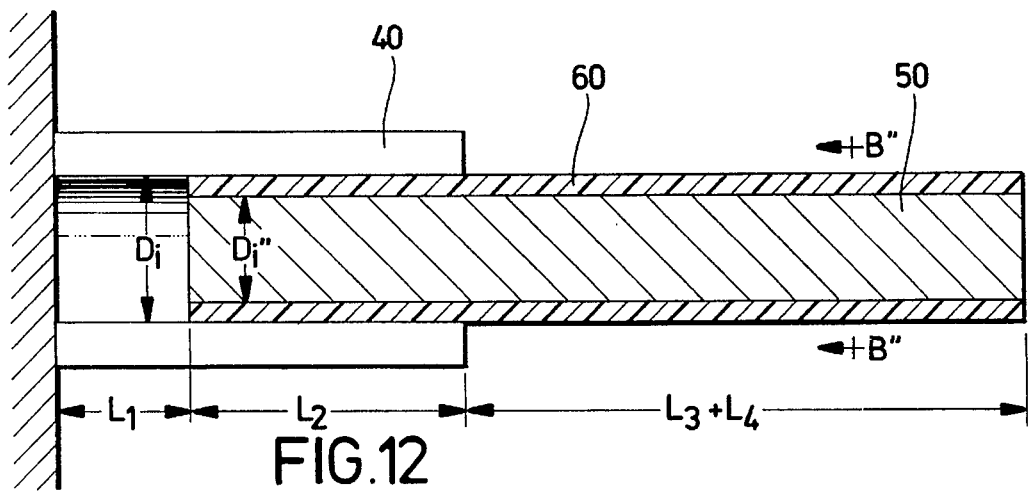
FIG. 12 is a side view of another mechanical idealization of a PMMA grouted metal hip implant.

Again, for comparison FIGS. 11 and 12 present idealized mechanical models for rotatory stiffness for a press-fit all metal system and a PMMA grouted system respectively. The rotatory stiffness for these structures are given respectively as:

$$S' = \frac{1}{\left[\dfrac{L_1}{E_b I_b}\right] + \left[\dfrac{L_2}{E_b I_b + E_m I_m'}\right] + \left[\dfrac{L_3 + L_4}{E_m I_m'}\right]}$$

$$S'' = \frac{1}{\left[\dfrac{L_1}{E_b I_b}\right] + \left[\dfrac{L_2}{E_b I_b + E_m I_m'' + E_p I_p}\right] + \left[\dfrac{L_3 + L_4}{E_m I_m'' + E_p I_p}\right]}$$

It is apparent that the ratio S/S' will always be less than 1 when $E_c<E_m$. However, it is known that grouted metal stems provide adequate rotatory stability; thus, it is another objective of the present invention to have the ratio S/S" as high as possible and preferably greater than 1; i.e., the rotatory stiffness of the metal composite system should be preferably at least as stiff as the all-metal system which is grouted in place with PMMA. To better define this criteria we consider the following typical values for the parameters defining the mechanical idealizations:

$D_o$=25 to 35 (mm) bone outer diameter $D_i$=12 to 22 (mm) bone inner diameter and Composite stem and Press fit metal stem diameter $D_i''=(D_i-4)$ (mm) Grouted metal stem diameter $L_1$=25 mm $L_2$=60 mm $L_3$=50 mm $L_4$=75 mm $E_b$=2.5 million psi $E_m$=16 million psi for Ti—6Al—4V alloy $E_p$=0.33 million psi The ratio S/S" was computed as a function of composite modulus up to 16 million psi, the modulus of Ti alloy, for a 25 mm and 35 mm bone outer diameter respectively. For each stem diameter there is a modulus $E_2$ such that the ratio S/S" is greater than 1 if $E_c$ is greater than $E_2$. We specify this criteria for the preferred lower limit on the modulus $E_c$ as:

$$E_c \geq E_2 \text{ where S/S''}=1 \text{ when } E_c=E_2.$$

The computed values of $E_1$ and $E_2$ were plotted as a function of stem diameter. The most preferred embodiments of the current invention have composite moduli which fall between these two curves at the given stem diameter. It is apparent that all the values in this most preferred range fall in the range 1 to 8 million psi so this forms a preferred range for the invention.

It will be apparent to those skilled in the art that more exact mechanical idealizations, e.g. those using three dimensional finite element analysis, can be used to define the most preferred range for composite modulus even more exactly than in the approximate analysis disclosed above.

Ultimately, the fatigue strength of the composite distal stem and the transition 30 will further constrain the exact details of the composite construction. Often, strength correlates positively with modulus; strength considerations may impose higher values for the composite modulus than specified in the preferred or most preferred range.

There are many ways to achieve a composite modulus in the preferred ranges of the invention. For example, the axial modulus of polyether-ether-ketone/graphite composites was computed as a function of angle for [±α] constructions. It is apparent that composite modulus in the range 0 to 16 million psi can be achieved for values of alpha greater than approximately 15 degrees. Modulus in the preferred range 1 to 8 million psi can be achieved for values of alpha greater than approximately 30 degrees. Other methods for achieving specific modulus values include changing the volume fraction of fiber reinforcement in the composite or changing the type of reinforcement, e.g., aramid instead of graphite.

The method for determining the preferred composite modulus above refers specifically to that part of the stem 14 which is exposed to bone. In certain embodiments, only the region 24 is exposed to bone. The region 22 interfaces with the metal body 20. In order to minimize the potential for wear between the region 22 of stem 14 and aperture 26 of body 20, the modulus of the composite comprising region 22 should be made as high as possible. One can, for example reduce the fiber angle alpha in the region 22 to increase the modulus. This may be accomplished by utilizing nonlinear winding or braiding paths.

EXAMPLE 1

In this example, preforms of Hercules Magnamite® Type IM6 dry fiber were braided so as to produce a stem. The braid design was such as to introduce a gradient in the modulus of the composite along the stem length. At the untapered region 24, which is adjacent to bone, a low modulus was formed for enhanced load transfer while at the tapered region 22, which is adjacent to the metal proximal body of the implant, a higher modulus was formed to minimize relative motion between the composite and the metal. In particular, the braid comprised eight layers with the following construction:

| Layer | # Braider Carriers | Braid Type | Braid Angle Taper | Braid Angle Distal |
|---|---|---|---|---|
| 1 | 16 | Biaxial | 18 | 45 |
| 2 | 32 | Biaxial | 15 | 45 |
| 3 | 32 | Biaxial | 12 | 45 |
| 4 | 32 | Triaxial | 12 | 45 |
| 5 | 32 | Triaxial | 15 | 45 |
| 6 | 32 | Triaxial | 13 | 45 |
| 7 | 32 | Triaxial | 15 | 45 |
| 8 | 64 | Triaxial | 15 | 45 |

After braiding the preform was inserted in a mold and a thermosetting resin (Dow Tactix™ 138 epoxy) was injected and then cured to produce the finished composite stem. Inspection of the dimensions of the structure showed that the process yields a true net shape part without need for finish machining. The distal stem diameter was 16 mm.

Strain gages were applied to one sample which was tested in a distally fixed loading configuration. The equivalent modulus of the distal portion of the stem was determined to be 4.7 million psi.

EXAMPLE 2

A composite structure was filament wound with a right circular cylindrical distal region and a male taper proximal region to be used in a modular femoral hip system where the tapered region 22 forms the metal to composite joint and the untapered region 24 resides in the femoral canal. A thermoplastic filament winding system was used; specifically, parts were wound on a McClean-Anderson W60 winder outfitted with a welding head. Parts were wound using preimpregnated Hercules Magnamite® Type AS4 graphite fiber. The composite matrix was Du Pont J2 polyamide.

A filament winding program was developed to produce a higher modulus in the proximal tapered region vs. the distal region as well as to insure complete coverage of the part shape. The higher modulus in the taper region is aimed at reducing metal-to-composite relative motion while the reduced modulus in the distal region is aimed at enhancing load transfer to surrounding bone.

Eleven filament wound layers comprise the part per the following table. Layers 1, 3, 6, 9 and 11 comprise 90 degree oriented fiber in both the tapered and distal regions. Layers 4, 7 and 10 comprise ±10 degree oriented fibers in both the tapered and distal regions. Layers 2, 5 and 8 are nonlinear winding layers generating ±20 angles in the taper region and ±55 degree angles in the distal region.

| Layer | Wind Angle Taper | Wind Angle Distal |
|---|---|---|
| 1 | 90 | 90 |
| 2 | 20 | 55 |
| 3 | 90 | 90 |

-continued

| Layer | Wind Angle | |
| --- | --- | --- |
| | Taper | Distal |
| 4 | 10 | 10 |
| 5 | 20 | 55 |
| 6 | 90 | 90 |
| 7 | 10 | 10 |
| 8 | 20 | 55 |
| 9 | 90 | 90 |
| 10 | 10 | 10 |
| 11 | 90 | 90 |

Filament wound structures were finished on a precision grinding lathe to achieve the desired tolerance on the external taper. The diameter of the distal stem was 14.8 mm. Strain gages were applied to one sample which was tested in a distally fixed loading configuration. The equivalent modulus of the distal portion of the stem was determined to be 6.8 million psi.

EXAMPLE 3

A [0, ±30,90] laminate comprising Hercules Magnamite® Type AS4 graphite fiber and Amoco's UDEL® 1700 polysulfone was formed by compression molding. The laminate was machined to a stem shape. The diameter of the distal stem was 16 mm. Strain gages were applied to one sample which was tested in a distally fixed loading configuration. The equivalent modulus of the distal portion of the stem was determined to be 9.5 million psi.

EXAMPLE 4

A composite structure was filament wound with a tapered exterior shape and an internal tapered region to be used in a modular tibial knee system as shown schematically in FIG. 3 where the internal tapered region 32 is integral to the metal to composite joint and the exteriorly tapered regions 22 and 24 reside in the tibial canal. A thermoplastic filament winding system was used; specifically, parts were wound on a McClean-Anderson W60 winder outfitted with a welding head. Parts were wound using preimpregnated Hercules Magnamite® Type AS4 graphite fiber. The composite matrix was UDEL® 1700 polysulfone.

The winding program comprised 9 nonlinear layers in which wind angle varied from 75 to 25 degrees moving from the larger to the smaller diameter of the external taper.

We claim:

1. An orthopedic device adapted for implantation within a body, the device comprising:
    an intraosseous metal portion; and
    an intraosseous composite portion of one or more layers and comprising (i) a first extension having a modulus and that is received within said metal portion and secured thereto and (ii) a second extension positioned outside said metal portion;
    said composite portion having a length and comprising one or more filaments disposed about a longitudinal axis by winding or braiding each filament along said length at winding or braiding angles with respect to the longitudinal axis selected to provide the second extension with a modulus that is less than the modulus of the first extension, the winding or braiding angle in some of the layers of the first extension being less than the winding or braiding angle in the same layers of the second extension, said filaments further being disposed within a polymer matrix.

2. The orthopedic device of claim 1 wherein the cross-sectional area of said first extension is different from the cross-sectional area of said second extension.

3. The orthopedic device of claim 1 wherein said first and second extensions are cylindrical.

4. The orthopedic device of claim 1 wherein said first extension forms a taper such that the cross-sectional area of said extension decreases proximally.

5. The orthopedic device of claim 4 wherein the maximum cross-sectional area of said first extension is different from the cross-sectional area of said second extension, said extensions being joined by a bevelled transition portion having a cross-sectional area equal to that of said first extension at the first extension-bevelled portion interface and a cross-sectional area equal to that of said second extension at the second extension-bevelled portion interface.

6. An orthopedic device adapted for implantation within a body, the device comprising:
    an intraosseous metal portion;
    an intraosseous composite portion of one or more layers and comprising a first extension having a modulus and that is received within said metal position and secured thereto and a second extension positioned outside said metal portion; and
    an intraosseous metal insert interposed there between and connecting said metal portion to said composite portion,
    said metal insert being received within said metal portion and frictionally secured thereto, said metal insert further forming a taper such that the cross-sectional area of said metal insert increases from a first end received within said metal portion and a second end connected to said composite portion, said metal insert further being connected to said composite portion by an adhesive joint or a shrink fit joint,
    said composite portion having a length and comprising one or more filaments disposed about a longitudinal axis by winding or braiding the filaments at winding or braiding angles with respect to the longitudinal axis selected to provide the second extension with a modulus that is less than the modulus of the first extension the winding or braiding angles in some of the layers of the first extension being less than the winding or braiding angle in the same layers of the second extension, said filaments further being disposed within a polymer matrix; and
    said intraosseous metal portion and said intraosseous composite portion adapted to contact the body.

7. The orthopedic device of claim 1 wherein the intraosseous metal portion is selected from the group consisting essentially of stainless steel, cobalt-chrome alloy, and titanium alloy.

8. The orthopedic device of claim 1 wherein the polymer matrix is selected from the group consisting essentially of polysulfone, polyether-ether-ketone, polyether-ketone-ketone, polyimide, epoxy, and polycyanate.

9. The orthopedic device of claim 1 wherein the filaments are selected from the group consisting essentially of carbon, graphite, glass, and aramid fiber.

10. The orthopedic device of claim 1 useful as a human hip implant wherein the intraosseous metal portion is a proximal metal body and the intraosseous composite portion is a distal composite stem.

11. The orthopedic device as defined in claim 1, said second extension having an equivalent flexural modulus, $E_c$, selected according to the criteria:

$E_c < E_1$ where $\sigma_b/\sigma_b''=1$ when $E_c=E_1$ and $E_c > E_2$ where $S/S''=1$ when $E_c=E_2$ wherein $\sigma_b$ is the maximum bending stress in the bone adjacent to the implanted device at the extension of the composite portion positioned outside of the metal portion; $\sigma_b''$ is the maximum bending stress in the bone adjacent to the implanted orthopedic device wherein the intraosseous portion is entirely metal affixed in place by polymethylmethacrylate bone cement; S is the rotatory stiffness of the implanted device including the composite portion and the metal portion; and S" is the rotatory stiffness of the implanted device of metal affixed with bone cement.

12. The orthopedic device as defined in claim 1, said composite portion having an equivalent flexural modulus of up to 16 million psi.

13. The orthopedic device as defined in claim 1, wherein the second extension has an equivalent flexural modulus of 1 million to 8 million psi.

* * * * *